(12) United States Patent
Lehtonen-Krause

(10) Patent No.: US 7,474,912 B2
(45) Date of Patent: Jan. 6, 2009

(54) METHOD AND MAGNETIC RESONANCE SYSTEM FOR GENERATION OF LOCALIZER SLICE IMAGES OF AN EXAMINATION VOLUME OF A SUBJECT

(75) Inventor: Sari Lehtonen-Krause, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 255 days.

(21) Appl. No.: 11/220,952

(22) Filed: Sep. 7, 2005

(65) Prior Publication Data

US 2006/0056674 A1 Mar. 16, 2006

(30) Foreign Application Priority Data

Sep. 7, 2004 (DE) ........................ 10 2004 043 263

(51) Int. Cl.
*A61B 5/05* (2006.01)

(52) U.S. Cl. ...................................................... 600/410

(58) Field of Classification Search .......... 600/407–480
See application file for complete search history.

(56) References Cited

U.S. PATENT DOCUMENTS

| | | | | |
|---|---|---|---|---|
| 6,108,573 | A * | 8/2000 | Debbins et al. | 600/410 |
| 6,725,077 | B1 * | 4/2004 | Balloni et al. | 600/410 |
| 6,757,417 | B2 * | 6/2004 | Licato et al. | 382/131 |
| 7,209,779 | B2 * | 4/2007 | Kaufman et al. | 600/425 |
| 2001/0007919 | A1 * | 7/2001 | Shahidi | 600/427 |
| 2002/0082494 | A1 * | 6/2002 | Balloni et al. | 600/410 |
| 2003/0004405 | A1 * | 1/2003 | Townsend et al. | 600/407 |
| 2003/0018245 | A1 * | 1/2003 | Kaufman et al. | 600/407 |
| 2004/0105574 | A1 | 6/2004 | Pfaff | |
| 2004/0161139 | A1 | 8/2004 | Samara et al. | |

FOREIGN PATENT DOCUMENTS

WO WO 00/72273 11/2000

OTHER PUBLICATIONS

"Prospective Registration of Human Head Magnetic Resonance Images for Reproducible Slice Positioning Using Localizer Images" Gedat et al, J. of Mag. Res. Imaging, vol. 20 (2004), pp. 581-587.

\* cited by examiner

*Primary Examiner*—Eric F Winakur
*Assistant Examiner*—Nasir Shahrestani
(74) *Attorney, Agent, or Firm*—Schiff Hardin LLP

(57) ABSTRACT

In a method and magnetic resonance (MR) system for generation of localizer slice images of an examination volume of a subject for MR examination planning, such as for a whole-body examination of a patient, the localizer slice images being in three orthogonal planes, image data for the entire examination volume and acquired in the form of a family of individual, plane-parallel slice images in a first designated plane orientation for generation of a 3D volume image data set, a two-dimensional coronal or sagittal representation of the entire examination volume in the first designated plane is generated using the slice image family and is output to a monitor, for following image data acquisitions, of a desired examination region is selected in the representation of the entire examination volume on the monitor and is represented on the monitor as a localizer slice image for the first plane and the second and third localizer slice images in the two further orthogonal planes are determined using the 3D volume image data of the selected examination region, and are represented on the monitor.

12 Claims, 2 Drawing Sheets

METHOD AND MAGNETIC RESONANCE SYSTEM FOR GENERATION OF LOCALIZER SLICE IMAGES OF AN EXAMINATION VOLUME OF A SUBJECT

BACKGROUND OF THE INVENTION

1. Field of the Invention

The present invention concerns a method for generating of localizer slice images of an examination volume of a subject for examination planning (in particular in a whole-body examination) with a magnetic resonance system, the localizer slice images being in three orthogonal planes.

2. Description of the Prior Art

For generation of image exposures in magnetic resonance tomography, the region to be examined must be brought into the homogenous central volume of the magnetic field. The size of the magnetic field central volume determines the size of the region that can be examined without requiring a movement of the table on which the patient lies. Overview images (known as localizer slice images) must initially be obtained for each individual scan region that, in currently typical systems, have a size of up to approximately 50 cm, and in fact must be measured for all three body axis orientations, therefore perpendicular to one another.

The planning of an examination is difficult, in particular when a number of examination regions are to be acquired (for example in a whole-body examination), since an overview of adjacent examination regions or the entire body of the patient does not occur in the planning phase. Only the current examination region is shown in the image segments that serve for planning, such that orientation thereof is difficult. In addition, for further examination planning the operator must wait for the acquisition of the three localizer slice images for the current examination region.

SUMMARY OF THE INVENTION

An object of the present invention is to provide a method that allows an improved generation of localizer slice images of an examination volume of a patient with a magnetic resonance system.

This object is achieved in accordance with the invention by a method for generation of localizer slice images of an examination volume of a patient for examination planning (in particular for a whole-body examination) with a magnetic resonance system, wherein the localizer slice images respectively are in three orthogonal planes, wherein image data for the entire examination volume are acquired in the form of a family of individual, plane-parallel slice images in a first designated plane orientation for generation of a 3D volume image data set, a two-dimensional coronal or sagittal representation of the entire examination volume generated in the first designated plane using the slice image family and is displayed at a monitor, for the following image data acquisitions, of a desired examination region in the representation of the entire examination volume on the monitor is selected and represented as a localizer slice image for the first plane on the monitor, and the second and third localizer slice images in the two further orthogonal planes are determined using the 3D volume image data of the selected examination region and are represented on the monitor.

The entire examination volume is initially acquired in individual, parallel slices of a specific thickness, for example directly upon entrance of the patient into the magnetic resonance system, so a more complete 3D volume image data set is acquired. For a designated plane, a two-dimensional representation of the entire examination volume is generated that, for example, can be the entire body or the upper body. Depending on the diagnostic purpose of the examination, a coronal or sagittal representation that is finally shown on a monitor (for example a display or the like) is advantageous. In principle a transversal representation is also possible, but this does not offer an overview of larger examination volumes.

Due to the output of the entire examination volume on the monitor, the operator of the magnetic resonance system (given an overview therewith provided of the entire existing region) can specifically select the desired examination region that is then shown on the monitor as a localizer slice image of the first plane. The second and third localizer slice images, thus (for example) the associated sagittal and transversal images given a coronal representation in the first plane, are calculated and shown using the 3D volume image data of the selected examination region that was acquired in the first step in the acquisition of the entire examination volume. Known computational programs for plane reconstruction can be used for this purpose.

With the inventive method, it is thus not necessary to initially acquire data for all three localizer slice images of the various body axis orientations after selection of an examination region. Rather, the acquisition of the entire examination volume implemented at the beginning suffices for examination planning in the first designated plane orientation, such that the number of data acquisition repetitions and (given selection of a suitable computer system for determination of the missing orthogonal planes) the examination time for the patient can be advantageously reduced.

For the operator, the planning of the examination is made significantly easier since, for selection of the following examination region, the operator always can refer to the representation of the entire examination volume in which already-examined regions can be particularly characterized, for example emphasized in color or surrounded by boxes. A structured planning is thus possible that starts from the entire examination volume in which the new examination regions can be selected, and wherein the still-missing localizer slice images can be immediately calculated and displayed.

The entire examination volume can inventively be acquired in coronal or sagittal orientation. Data acquisition for the coronal orientation is preferable in present magnetic resonance systems since a faster measurement is thus possible. A sagittal data acquisition alternatively can be implemented dependent on the total volume to be examined and on the goal of the examination.

The representation of the entire examination volume can be composed of adjacent or overlapped data sets from a number of exposures (scans) (in particular overlapping in regions) of an orientation. The data acquisitions with the magnetic resonance system must ensue in the magnetic field center; in present systems in a region with a diameter of up to 50 cm. Given a whole-body examination it is necessary to combine a number of exposures (for example four or five) for acquisition of the entire examination volume using plane-parallel slice image families. An overlapping between the exposures in the range of a few centimeters ensures that the volume is actually completely acquired. The correct composition or overlapping for display can ensue using the data of the magnetic resonance system or by image recognition algorithms executed in a control and processing device.

The first designated plane for representation of the entire examination volume can be pre-established or can be selected by a user. Thus, for example, by default the tenth or twentieth plane can be selected, or even a median plane. This established standard plane can be different for different standard examinations (for example to be input via the monitor). In special examinations or given the presence of anatomical peculiarities, the user can select (for example via input on the monitor) the designated plane to be used for representation depending on the purpose and goal of the examination.

The examination region in the representation of the entire examination volume is advantageously selected by means of a freely positionable selection tool (in particular a selection box) via an operating device. Such an operating device can be a computer mouse, a keyboard, a joystick or the like. The user can shift the selection tool before the actual selection, whereby the user receives an impression of the selectable examination region. The selection tool (for example the box) can be changed in terms of size (for example by dragging) in the framework of the possibilities for image acquisition that the magnetic resonance system offers. The selection can likewise be determined by clicking on specific vertices (corner points) or on a middle point relevant for the acquisition.

In an embodiment of the invention provides that the first localizer slice image is shown enlarged in comparison with the entire examination volume. For example, it can be shown with the same size as the typical localizer slice images conventionally acquired only for one examination region. The enlargement can be adjustable to ensure an optimal examination planning by the operator of the system.

The representation of the second and third localizer slice images ensues by means of established section lines (in particular determined via the centerlines of the first localizer slice image) or by means of three-dimensional section lines that can be selected by the user. It is thus possible to set a default calculation of the missing localizer slice images, preferably oriented on the centerlines, but the user also can determine (for example by the use of virtual rules (guides; straight edges) which lines should be used for the calculation of the missing localizer slice images. The separate selection by the user is particularly useful when the selection of the examination region with regard to the middle point of the selection tool might not ensue with sufficient precision in the smaller representation of the entire examination volume.

The above object also is achieved in accordance with the invention by a magnetic resonance system that is fashioned for implementation of the method described above.

DESCRIPTION OF THE PREFERRED EMBODIMENTS

Figure 1:
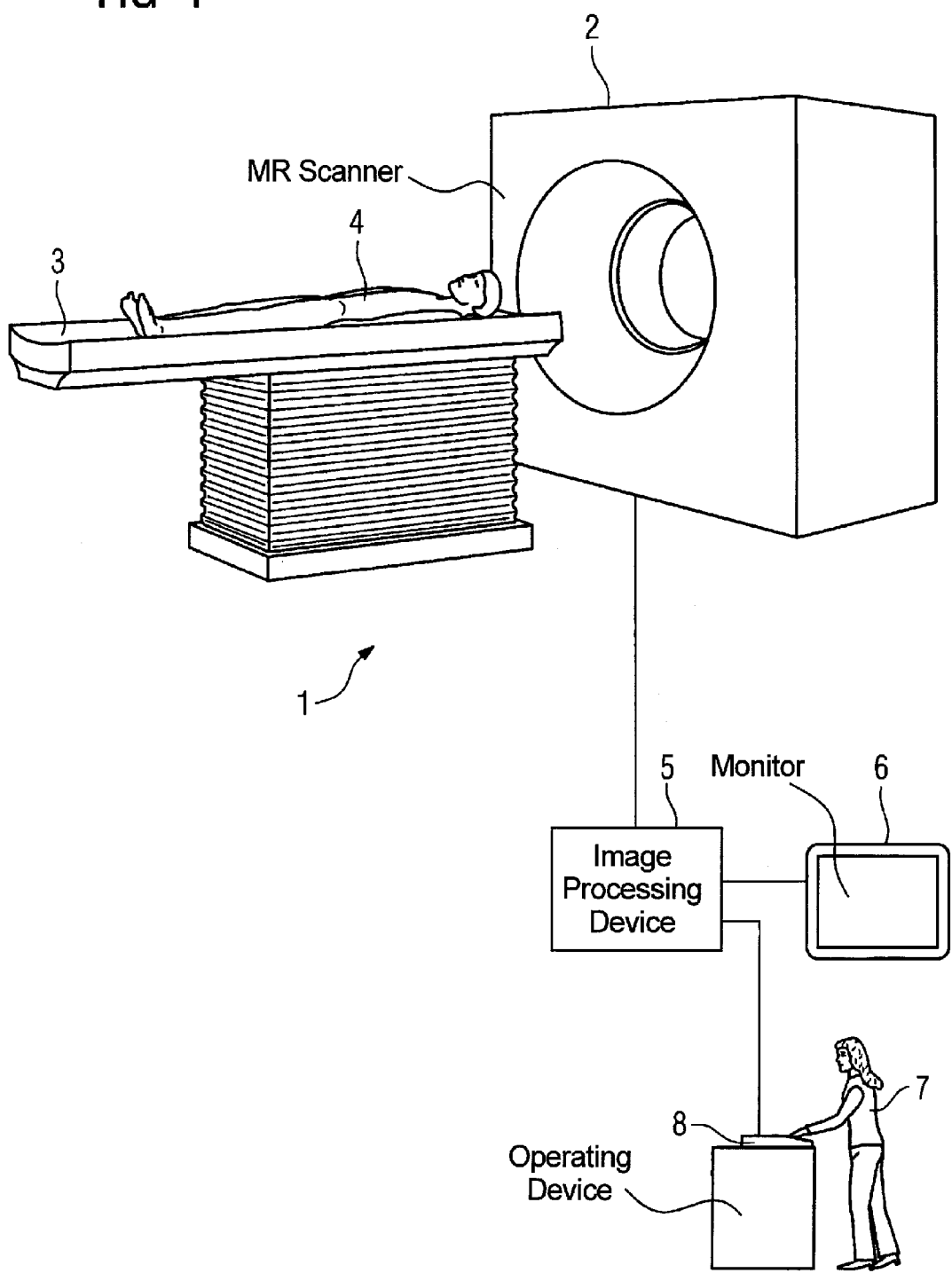
FIG. 1 is a schematic block diagram of an inventive magnetic resonance system.

FIG. 1 shows an inventive magnetic resonance system 1 that includes a magnetic resonance scanner 2 as well as a patient table 3 on which a patient 4 is positioned. The system 1 also has a control and processing device 5 that serves for control of the system 1 and that includes a microprocessor for processing of the acquired image data. The data processed by the control and processing device 5 are shown on a monitor 6. Operation of the magnetic resonance system 1 by a user 7 ensues via an operating device 8 (for example a keyboard and a mouse) communicating with the control and processing device 5.

A whole-body examination can serve to detect metastases, to acquire an overview of the state of the blood vessels given vessel diseases, or to check the skeleton status in the context of bone diseases. Such a whole-body examination can be implemented with the inventive magnetic resonance system 1, by moving the patient table 3 with the patient 4 into the magnetic resonance scanner 2, whereby image data of body of the patient 4 are acquired in a first plane orientation (preferably coronal). The data acquisition ensues in the inventive magnetic resonance system 1 such that a family of plane-parallel slice images corresponding to the size of the center region suitable for data acquisition is acquired in the magnetic field center, a measurement volume being available with a diameter of approximately ten centimeters. The patient 4 is subsequently moved somewhat further into the magnetic resonance scanner 2 with the patient table 3, such that the next family of plane-parallel slice images can be acquired.

The image exposures are subsequently processed in the control and processing device 5 so that a two-dimensional representation of the entire examination volume can be obtained by combining the individual exposures and shown on the monitor 6. This display on the monitor 6 allows the user 7 to select a desired examination region via the operating device 8, the desired examination region then being shown on the monitor 6 enlarged by the control and processing device 5 as a localizer slice image of a plane previously determined (if applicable) by the user 7 with the operating device 8.

Using the 3D volume image data that are known from the exposure of the entire examination volume, the control and processing device 5 calculates the missing localizer slice image (thus the missing sagiftal and transversal image with regard to a coronal image). If applicable the user 7 can select, via the operating device 8, the relevant section lines for the calculation of the missing orientations beforehand in the representation of the first localizer slice image.

Figure 2:
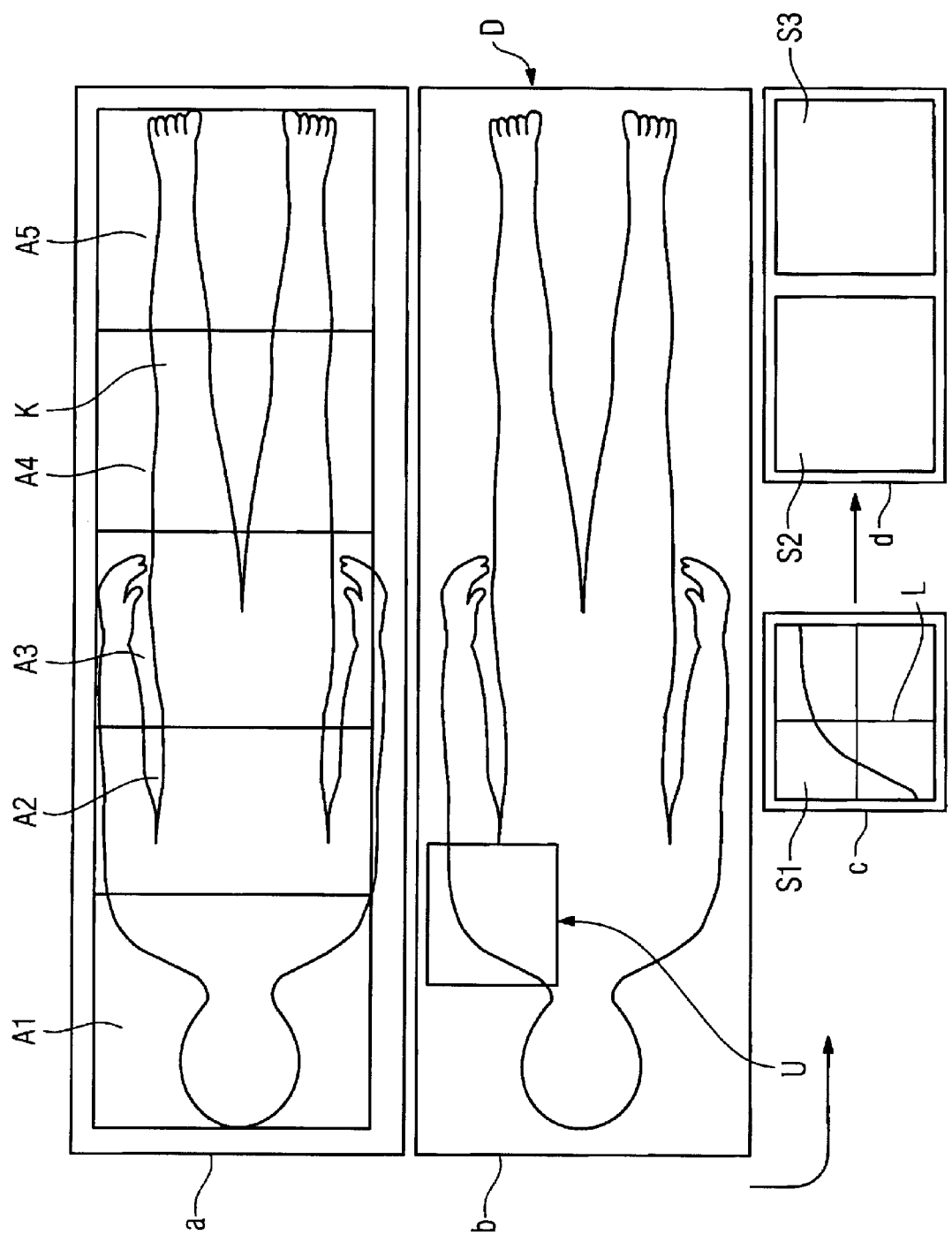
FIG. 2 schematically illustrates an embodiment of the inventive method.

FIG. 2 shows a workflow illustration of an inventive method. In step a, an acquisition of the entire examination volume (here the entire body K of a patient) is initially conducted, the acquisition ensuing with plane-parallel slice images in a coronal orientation.

The exposures A1 through A5 are respectively acquired for regions of the examination volume shifted in the direction of the coronal axis of the body K, the size of which regions of the examination volume is determined by the homogeneous center of the magnetic field. With each exposure A1 through A5, a family of plane-parallel slice images is determined that acquires the examination volume in the direction of the sagittal axis with a predetermined slice thickness. A complete, three-dimensional volume image data set of the body K thus is acquired.

A two-dimensional coronal representation D of the examination volume (here of the body K) in a first designated plane (which here corresponds to that already shown in step a) then ensues in step b. This plane can be preset (for example dependent on an examination to be established) or it can be selected for special examinations or on the part of a user given anatomical peculiarities. The selection of a desired examination region U (that, in the shown case, corresponds to the shoulder region) subsequently ensues in the monitor representation.

The selected examination region U is shown enlarged on the monitor as a localizer slice image S1 of the first plane in a step c. In the enlarged representation of the first localizer slice image, with a selection tool (for example a virtual rule) the user selects the section lines L that should be decisive for the missing sagittal and transversal localizer slice image.

In a subsequent step d, the second and third localizer slice image S2 and S3 are calculated corresponding to the selection of the user using the 3D volume image data that is available from the acquisition of the entire examination volume and are likewise shown on the monitor.

A further examination region can be subsequently selected in step b, either after the end of the exposures relevant for the first examination region or also beforehand, again using the representation D of the body. The examination regions U that were already selected in a previous pass of the step b thereby remain advantageously emphasized in the representation D, for example via a different color presentation or a hatching of the selection box. The new examination region U is in turn shown enlarged as a first localizer slice image S1 given a new repetition of the step c. The determination of the section lines L relevant for the second and third localizer slice images in turn ensues by means of virtual rules. The missing localizer slice images S2 and S3 are shown in step d.

The inventive method thus offers at any time an overview of the entire examination volume, whereby the planning is significantly simplified in a longer examination. It is no longer necessary to measure the localizer slice images of all three orientations for each new selected examination region; the acquisition of the entire examination volume at the beginning of the examination is sufficient. Errors in the implementation of measurements, for example forgetting specific acquisitions or a double-acquisition such as a two-time acquisition of localizer images of a region, can be prevented; and the examination can overall be implemented faster due to the easier orientation of the user, such that the residence time of the patient in the system can be reduced and, if applicable, a larger number of patients can be examined with the system.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A method for generating magnetic resonance localizer slice images of an examination volume of a subject in a magnetic resonance system for examination planning, said localizer slice images respectively being in three orthogonal planes, comprising the steps of:
   acquiring a 3D volume image data set of an entire examination region of a subject in a magnetic resonance scanner, as a family of individual, plane-parallel slice images in a first designated plane orientation from among said three planes;
   generating a two-dimensional representation of said entire examination volume, selected from the group consisting of a coronal representation and a sagittal representation, in said first designated plane orientation using said slice family, and displaying said two dimensional representation on a monitor;
   selecting a selected examination region in said entire examination volume from said two dimensional representation displayed at said monitor, and representing said selected examination region as a first of said localizer slice images in said first designated plane orientation on said monitor; and
   automatically electronically determining a second and a third of said localizer slice images respectively in two remaining planes of said three planes, using said 3D volume image data of the selected examination region, and representing said second and third of said localizer slice images on said monitor.

2. A method as claimed in claim 1 comprising acquiring image data from said entire examination region in a coronal orientation.

3. A method as claimed in claim 1 comprising acquiring image data from said entire examination region in a sagittal orientation.

4. A method as claimed in claim 1 comprising acquiring said 3D volume image data set as a plurality of exposures each representing a portion of said entire examination volume, and overlapping said plurality of exposures to form said 3D volume image data set of said entire examination volume.

5. A method as claimed in claim 1 comprising allowing manual designation of said first designated plane orientation.

6. A method as claimed in claim 1 comprising providing a manually operable selection tool allowing manual interaction with said two-dimensional representation on said monitor, and manually selecting said selected examination region using said selection tool.

7. A method as claimed in claim 6 wherein said selection tool comprises a selection box, and comprising selecting said selected examination region by moving said selection box to a selected position within said two-dimensional representation on said monitor.

8. A method as claimed in claim 1 comprising displaying said first of said localizer slice images on said monitor in an enlarged representation in comparison to said entire examination volume.

9. A method as claimed in claim 1 comprising representing said second and said third of said localizer slice images by establishing three-dimensional section lines of said first of said localizer slice images.

10. A method as claimed in claim 9 comprising employing automatically, electronically determined median lines of said first of said localizer slice images as said three-dimensional section lines.

11. A method as claimed in claim 9 comprising allowing free, manual establishment of said three-dimensional section lines.

12. A magnetic resonance examination system for generation of magnetic resonance localizer slice images of an examination volume of a subject for examination planning, said localizer slice images respectively being in three orthogonal planes, comprising:
   a magnetic resonance scanner adapted to receive an examination subject therein;
   a computer connected to said magnetic resonance scanner for operating said magnetic resonance scanner, said computer having a monitor connected thereto; and
   said computer configured to operate said magnetic resonance scanner to acquire a 3D volume image data set of an entire examination region of a subject in the magnetic resonance scanner, as a family of individual, plane-parallel slice images in a first designated plane orientation from among said three planes, and said computer generating a two-dimensional representation of said entire examination volume, selected from the group consisting of a coronal representation and a sagittal representation, in said first designated plane orientation using said slice family, and displaying said two dimensional representation on said monitor, said computer allowing selection of a selected examination region in said entire examination volume from said two dimensional representation displayed at said monitor, and representing said selected examination region as a first of said localizer slice images in said first designated plane orientation on said monitor, and said computer automatically electronically determining a second and a third of said localizer slice images respectively in two remaining planes of said three planes, using said 3D volume image data of the selected examination region, and representing said second and third of said localizer slice images on said monitor.

* * * * *